US006878940B2

(12) United States Patent
Nakamura et al.

(10) Patent No.: US 6,878,940 B2
(45) Date of Patent: Apr. 12, 2005

(54) METHOD AND APPARATUS FOR INFRARED GAS ANALYSIS (75) Inventors: Hiroshi Nakamura, Kyoto (JP); Masayuki Adachi, Kyoto (JP)

(73) Assignee: Horiba, Ltd., Kyoto (JP)

( * ) Notice: Subject to any disclaimer, the term of this patent is extended or adjusted under 35 U.S.C. 154(b) by 178 days.

(21) Appl. No.: 10/251,676

(22) Filed: Sep. 21, 2002

(65) Prior Publication Data

US 2003/0071218 A1 Apr. 17, 2003

(30) Foreign Application Priority Data

Sep. 27, 2001 (JP) .......................................... 2001-297125
Jan. 25, 2002 (JP) .......................................... 2002-016647

(51) Int. Cl.[7] .............................................. G01N 21/59
(52) U.S. Cl. ........................................................ 250/343
(58) Field of Search ................................. 250/343, 344, 250/345, 346, 341.5, 339.1

(56) References Cited

U.S. PATENT DOCUMENTS 3,979,589 A * 9/1976 Sternberg et al. ......... 250/252.1
5,600,142 A * 2/1997 Van Den Berg et al. .................... 250/339.13

* cited by examiner

Primary Examiner—David Porta
Assistant Examiner—Faye Polyzos
(74) Attorney, Agent, or Firm—Brooks Kushman P.C.

(57) ABSTRACT

A method and apparatus for infrared gas analysis are provided. The method includes measuring a concentration of a component in the sample gas, and measuring a concentration of water in the sample gas. The component concentration measurement is corrected with respect to water interference at a zero point. The component concentration measurement is further corrected with respect to water influence in coexistence to determine a corrected measurement that is corrected with respect to water interference at the zero point and water influence in coexistence.

14 Claims, 10 Drawing Sheets

PRIOR ART

METHOD AND APPARATUS FOR INFRARED GAS ANALYSIS

BACKGROUND OF THE INVENTION

1. Field of the Invention

The present invention relates to a method and apparatus for infrared gas analysis.

2. Background Art

Figure 10:
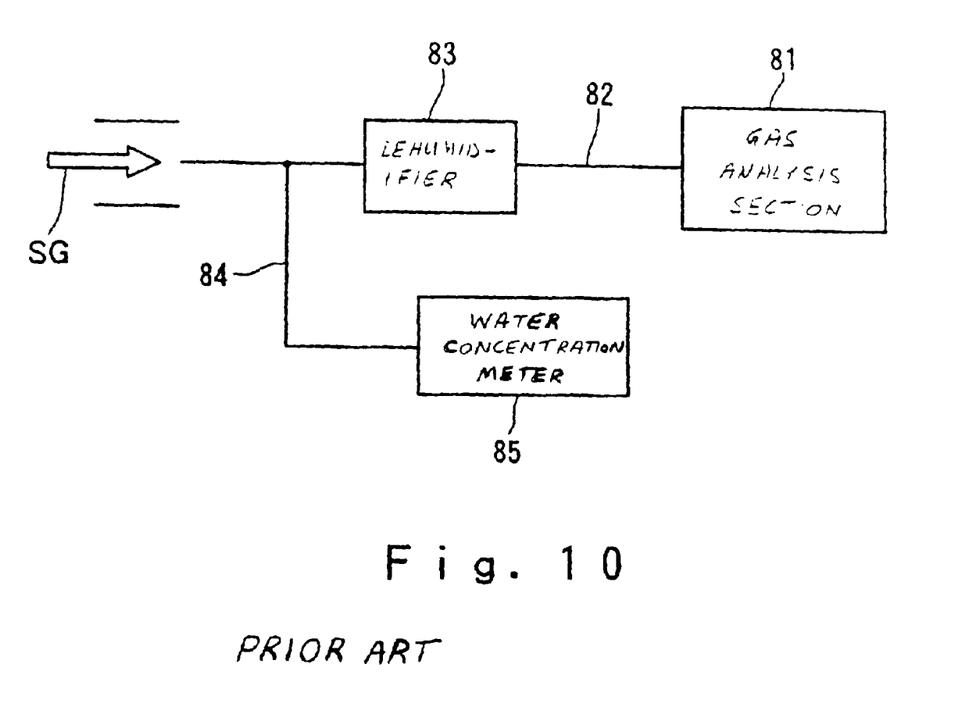
FIG. 10 is a diagram for describing a prior art.

In an apparatus for infrared gas analysis, a dehumidifier 83 such as an electronic cooling device, as shown in FIG. 10, has been heretofore provided in a feed line 82 of a sample gas SG for a gas analysis section 81 to dehumidify the sample gas SG and to feed the dehumidified sample gas SG to the gas analysis section 81 since a necessity exists for suppressing an influence of water included in the sample gas to the lowest level possible, when measurement is performed of a concentration of a specific component to be measured (a gas to be measured) that is included in the sample gas.

In a prior art method, however, not only was a construction of the entire measurement system more complex due to installment of the dehumidifier 83 therein, but hardship was also encountered in measurement of a gas with a high solubility in water. Furthermore, in the above construction, since measurement is performed after removal of water in the sample gas SG, a concentration of a component to be measured in the sample gas SG is raised by a value corresponding to a partial pressure of the water; therefore, a necessity arises for a correction with respect to a water partial pressure after the measurement.

In this case, as shown in FIG. 10, there arise requirements that a flow path 84 is connected to the sample gas line 82 so as to be branched therefrom upstream of the dehumidifier 83 of the sample gas line 82 and a water concentration meter 85 is provided in the branch flow path 84 to measure a water concentration included in the sample gas before dehumidification, or alternatively, that if no water concentration meter 85 is provided, a water concentration is estimated.

Even though a correction with respect to a water partial pressure is performed as described above, however, a correct concentration of a component to be measured has always been unable to achieve.

Meanwhile, in recent years, a problem of control on gas exhausted from an engine of a vehicle such as an automobile in running has increasingly drawn great attention and an importance has increased of grasping a quantity and concentration of the exhaust gas with certainty in order to preserve or protect the global environment. In a case where the dehumidifier 83 is installed as described above, however, since the entire measurement system becomes bulky, a great difficulty arises in mounting the apparatus for infrared gas analysis in a vehicle with a limited space available therein and the installment of a dehumidifier 83 itself results in cost up of the measurement system as a whole.

SUMMARY OF THE INVENTION

It is accordingly an object of the present invention to provide a method and apparatus for infrared gas analysis capable of performing correction with respect to an influence of water included in a sample gas, though with a simple construction adopted, to measure a concentration of a desired component to be measured with good precision.

In carrying out the present invention, a method and apparatus for infrared gas analysis of the present invention, in order to achieve the above object, includes: a gas analysis section installed with an infrared source at one end side of a cell and a detection section at the other end side thereof, wherein a sample gas is fed to the gas analysis section, not only a concentration of a component to be measured in the sample gas is measured but also a concentration of water included in the above-mentioned sample gas is measured, correction of a concentration of the above-mentioned component to be measured is first performed with respect to a water interference at a zero point and thereafter, a correction of the concentration of the above-mentioned component to be measured is performed with respect to an influence of water in coexistence, thereby acquiring a concentration of the component to be measured corrected with respect to an influence of water.

In the method and apparatus for infrared gas analysis, there can be performed a concentration measurement with a high precision from which a water interference and a water coexistence influence are removed. Dissimilar to a method and apparatus for infrared gas analysis in the prior art, since no necessity arises for a pretreatment device such as a dehumidifier to be installed, not only a response speed in analysis is faster by a value corresponding thereto, but a construction of the apparatus as a whole becomes compact to save a space, thereby enabling measurement at a low cost while saving power consumption. In addition, a gas to be measured including water at a high concentration can be measured directly without dehumidification.

Further, in carrying out the present invention, as a method and apparatus for infrared gas analysis of the present invention, a construction may be adopted in which two openings are formed in a pipe through which a sample gas flows, an infrared source is installed so as to face one opening thereof, while a detection section is installed at the other opening thereof, not only a concentration of a component to be measured in the above-mentioned sample gas is measured but also a concentration of water included in the above-mentioned sample gas is measured on the basis of detection outputs obtained when the above-mentioned sample gas is irradiated with an infrared beam, correction of a concentration of the above-mentioned component to be measured is first performed with respect to a water interference at a zero point and thereafter, a correction of the above-mentioned concentration of the component to be measured is performed with respect to an influence of water in coexistence, thereby acquiring a concentration of the component to be measured corrected with respect to an influence of water.

In the method and apparatus for infrared gas analysis, an air curtain may be formed outside an opening and in such a case, not only an optical window is unnecessary to install at the opening, but the sample gas leaking out from the opening, if any, would also be eliminated in a short time by the air curtain. Furthermore, in the method and apparatus, an optical window with infrared transmissability may be installed at an opening and in such a case, leakage of the sample gas from the opening to outside can be effectively prevented.

Still further, in carrying out the present invention, a method and apparatus for infrared gas analysis of the present invention, a construction may be adopted in which an infrared source emitting an infrared beam and a detection section receiving the infrared beam emitted from the infrared source are installed such that the infrared beam traverses the sample gas, not only a concentration of a component to be measured in the above-mentioned sample gas is measured but also a concentration of water included in the above-mentioned sample gas is measured, correction of a concentration of the above-mentioned component to be measured is first performed with respect to a water interference at a zero point and thereafter, a correction of the above-mentioned concentration of the component to be measured is performed with respect to an influence of water in coexistence, thereby acquiring a concentration of the component to be measured corrected with respect to an influence of water.

In any method and apparatus of the above methods and apparatuses for infrared gas analysis, concentrations of the component to be measured and water may be measured on one gas analysis section and in such a case, not only a delay time for correction is cancelled, but constitute members are reduced in number.

DETAILED DESCRIPTION OF THE PREFERRED EMBODIMENTS

Figure 1:
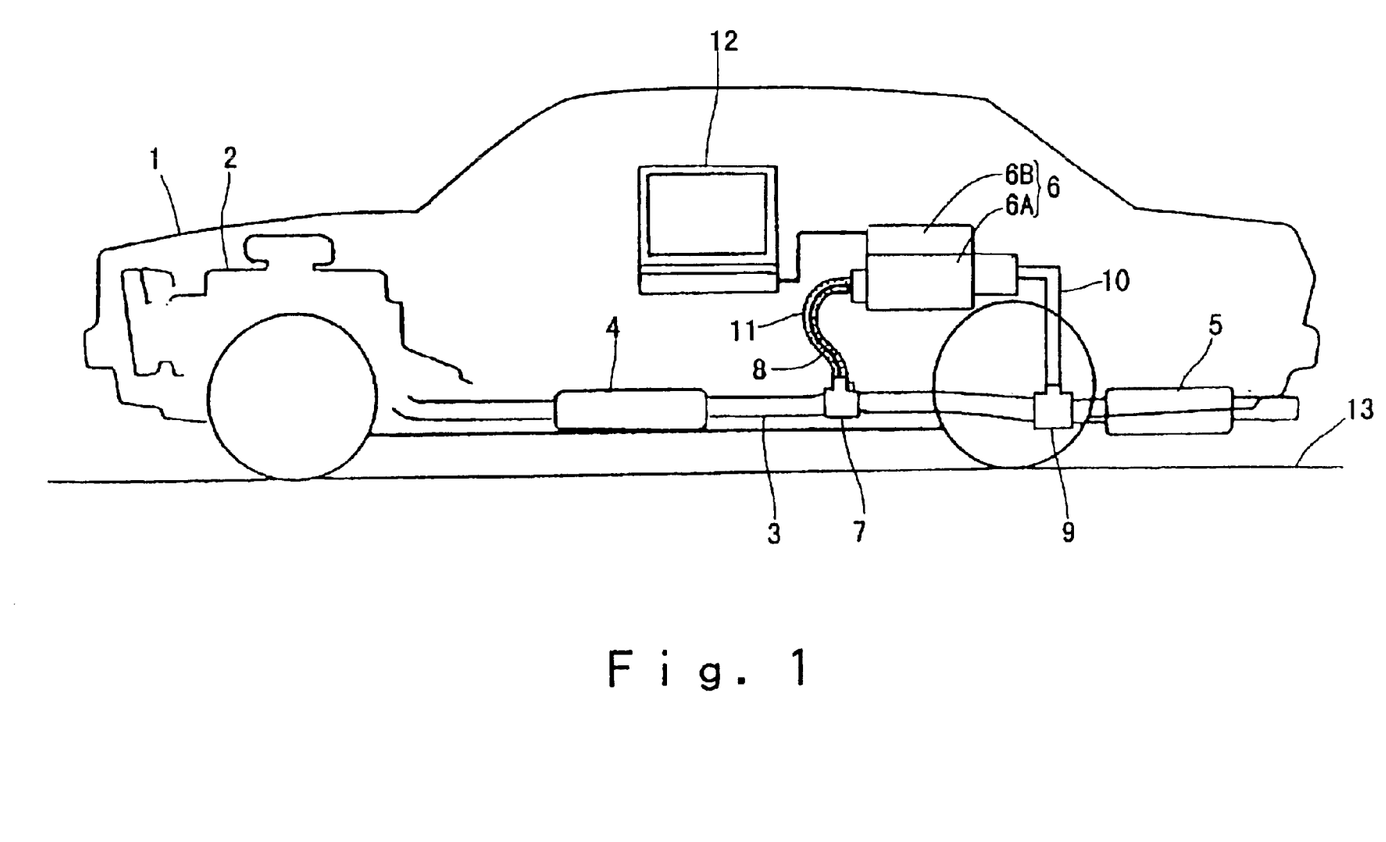
FIG. 1 is a view showing a state where an apparatus for infrared gas analysis is mounted in an automobile in a first embodiment of the present invention.

Description will be given of details of the present invention below with reference to the accompanying drawings. FIGS. 1 to 5 show the first embodiment of the present invention and FIGS. 1 to 3, at first, show an example apparatus for infrared gas analysis of the present invention. FIG. 1 shows an embodiment in which an apparatus for infrared gas analysis of the present invention is mounted in an automobile and in this Figure, a reference numeral 1 indicates an automobile (for example, an automobile during its use), a reference numeral 2, for example, is a diesel engine (hereinafter simply referred to as an engine), a reference numeral 3 is an exhaust pipe connected to the engine 2, and reference numerals 4 and 5 are a catalyst device and a muffler provided in the exhaust pipe 3.

A reference numeral 6 indicates an apparatus for infrared gas analysis (a construction of which will be described later) and is constructed of a gas analysis section 6A and an arithmetic operation and control section 6B. Connected to the gas analysis section 6A are a gas sampling flow path 8 having a proper branch connecting section 7 in the exhaust pipe 3 and an exhaust path flow 10 having a proper converge connecting section 9 in the exhaust pipe 3. In the example shown in the Figure, the branch connecting section 7 and the converge connecting section 9 are provided between the catalyst device 4 and the muffler 5 in the exhaust pipe 3 in the order. The branch connecting section 7 is constructed such that part of an exhaust gas flowing through the exhaust pipe 3 from the engine 2 is sampled. The gas sampling flow path 8 is wound on and along the whole length thereof including the branch connecting section 7 with, for example, a heater 11 such that the exhaust gas (the sample gas) flowing therethrough is heated and thermally insulated at a prescribed temperature. In such a way, since the sample gas is fed through the heated gas flow path without dehumidifying the sample gas, a gas to be measured including water at a high concentration can be measured without dehumidifying the gas. Furthermore, the arithmetic operation and control section 6B is constructed such that sections of the gas analysis section 6A are controlled according to instructions from a personal computer 12 mounted in the automobile 1 and a concentration arithmetic operation is performed on the basis of output signals of detectors (described later) of the gas analysis section 6A.

The personal computer 12 supplies/receives a signal to/from the arithmetic operation and control section 6B to control the entire apparatus for infrared gas analysis 6, to display a result of measurement on the basis of a signal from the arithmetic operation and control section 6B and store the result of measurement as data. Note that in FIG. 1, a reference numeral 13 indicates a road surface.

Figure 2:
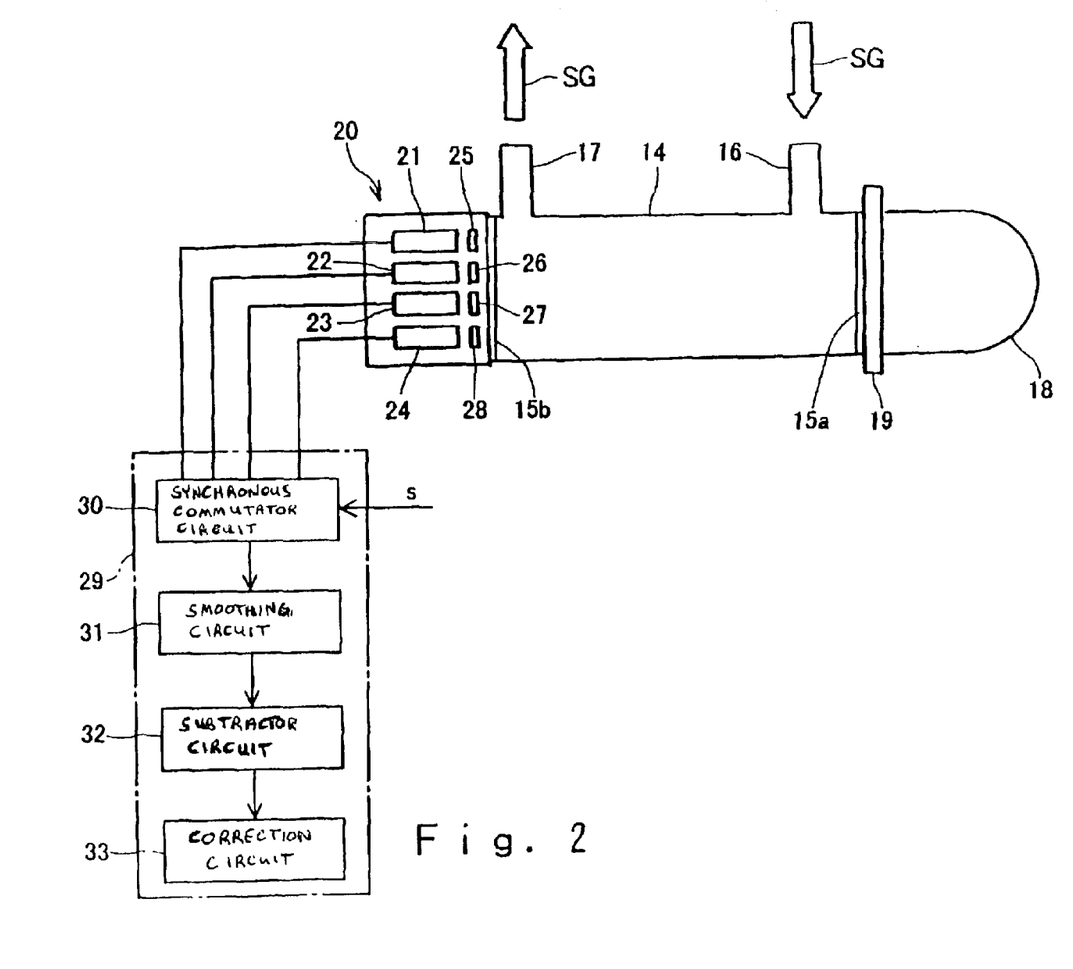
FIG. 2 is a view schematically showing an example construction of a gas analysis section in the above-mentioned apparatus for infrared gas analysis.

FIG. 2 shows schematically an example construction of the gas analysis section 6A of the apparatus for infrared gas analysis 6, in which Figure a reference numeral 14 indicates a cell and not only the cell 14 is sealed with cell windows 15a and 15b having infrared transmissability at both end sides thereof, but an inlet 16 and outlet 17 for the sample gas SG are formed. An end downstream of the gas sampling flow path 8 is connected to the gas inlet 16, while an end upstream of the exhaust flow path 10 is connected to the gas outlet 17.

A reference numeral 18 is an infrared source, provided in the one cell window 15a side of the cell 14, and for irradiating a space inside the cell 14 with an infrared beam, and a reference numeral 19 is a light chopper inserted between the infrared source 18 and the cell 14, which is rotated by, for example, a motor (not shown) to chop a infrared beam emitted from the infrared source 18 at a cycle.

Figure 3:
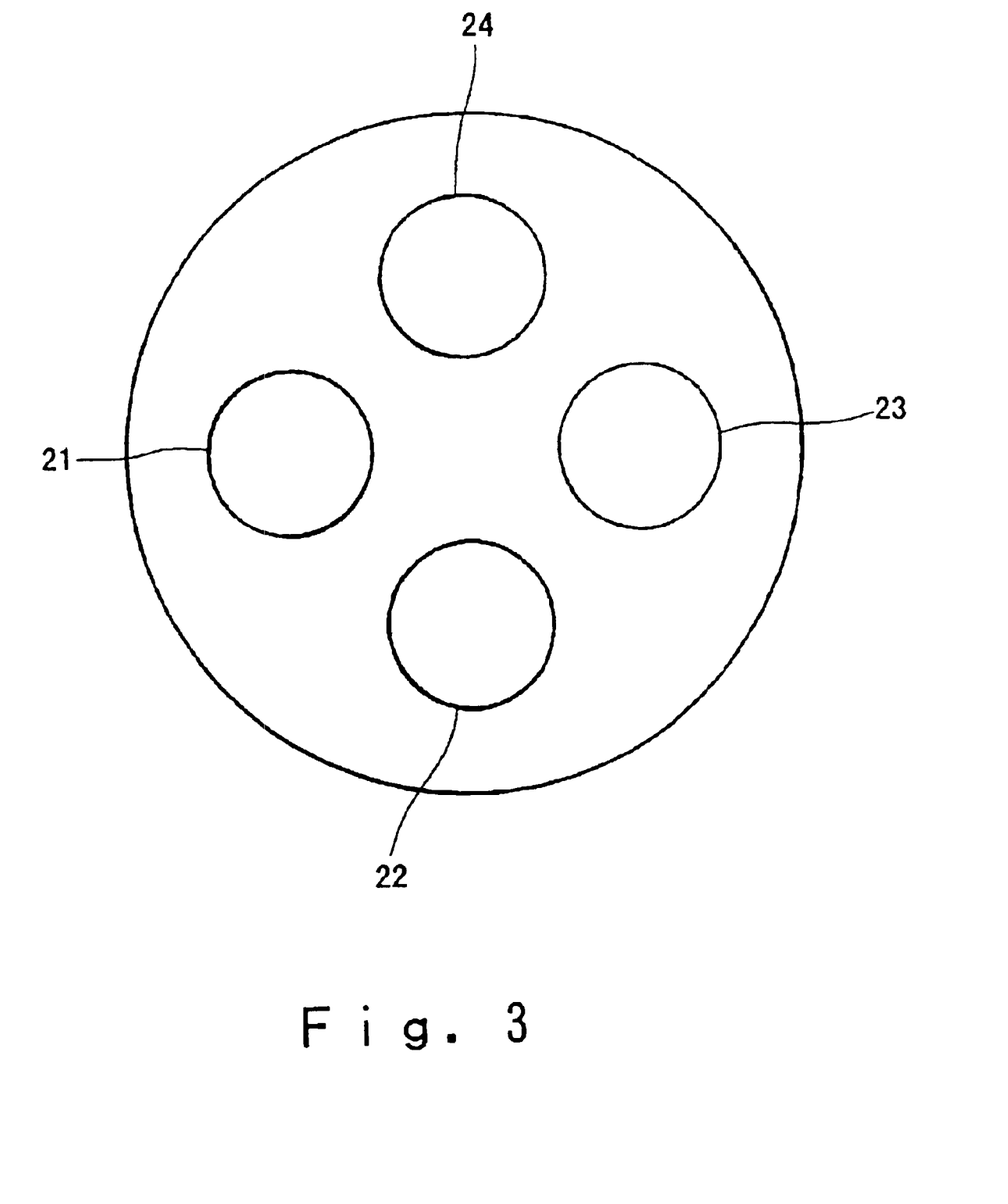
FIG. 3 is a view, as a model, showing an example arrangement of infrared detectors in a detection section of the above-mentioned gas analysis section.

A reference numeral 20 is a detection section provided in the other cell window 15b side of the cell 14, which is constructed of an optically parallel arrangement of plural infrared detectors. In this embodiment, for example, the detection section 20 is constructed: of a CO detector and a $CO_2$ detector for measuring CO and $CO_2$ respectively, which are components to be measured included in the sample gas SG; a water detector for measuring water ($H_2O$) as an interference component included in the sample gas SG; and as a comparison detector, as shown in FIG. 3, the four infrared detectors (hereinafter simply referred detectors) 21, 22, 23 and 24 (for convenience of description, depicted in arrangement on a straight line in FIG. 2) being provided at points on the same circle obtained by dividing the circle into four equal circumferential division lengths; and optical filters 25 to 28 provided correspondingly to the infrared detectors 21, 22, 23 and 24 on the light receiving side thereof.

The detectors 21 to 24 are constituted of, for example, semiconductor detectors and the optical filters 25 to 27 corresponding to the CO detector, $CO_2$ detector and water detectors 21 to 23 are constituted of band pass filters transmitting infrared only in respective characteristic absorption bands, the optical filter 25 corresponding to the CO detector 21 is constituted of a band pass filter transmitting infrared only in a characteristic absorption band of CO, the optical filter 26 corresponding to the $CO_2$ detector 22 is constituted of a band pass filter transmitting infrared only in a characteristic absorption band of the $CO_2$ and the optical filter 27 corresponding to the water detector 23 is constituted of a band pass filter transmitting infrared only in a characteristic absorption band of $H_2O$. The filter 28 corresponding to the comparison detector 24 is constituted of a band pass filter transmitting infrared with a wavelength in a band not overlapping any of the characteristic absorption bands of CO, $CO_2$ and $H_2O$ in the sample gas.

Figure 4:
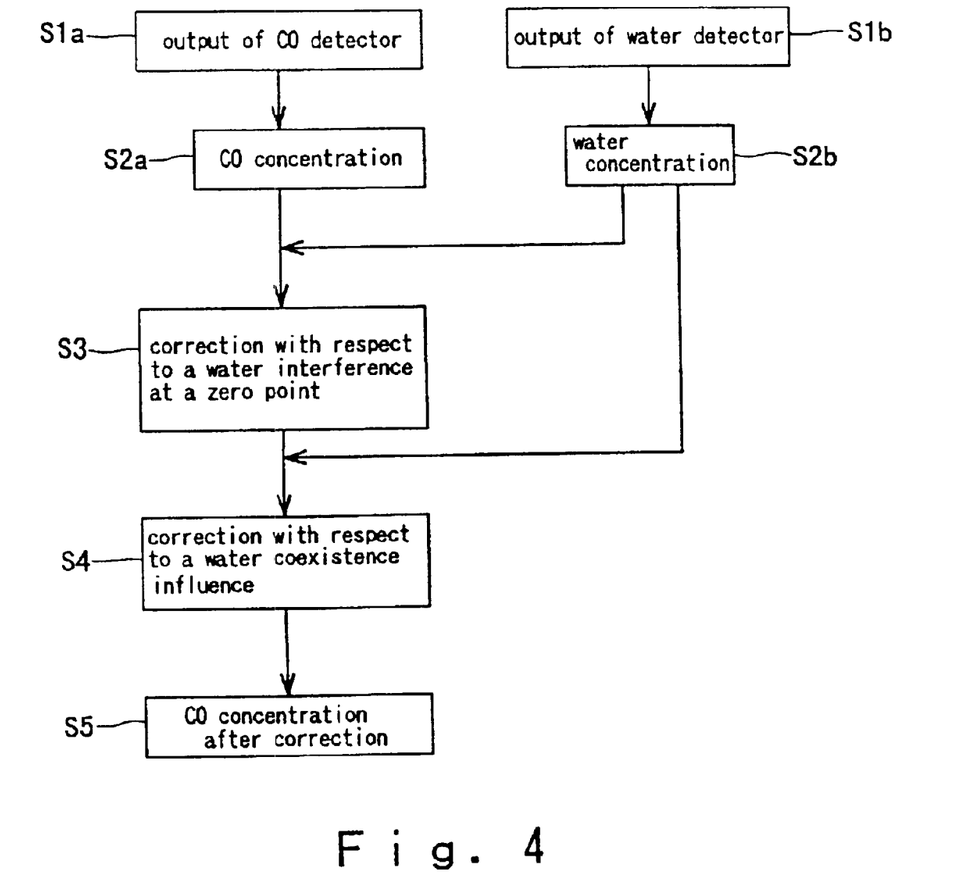
FIG. 4 is a flow chart showing an example correction procedure for a water interference influence performed in the above-mentioned apparatus for infrared gas analysis.

A reference numeral 29 indicates a concentration arithmetic operation section in the arithmetic operation and control section 6B, which performs a concentration arithmetic operation on the basis of outputs of the detectors 21 to 24, a reference numeral 30 is a synchronous commutator circuit, a reference numeral 31 is a smoothing circuit, a reference numeral 32 is a subtractor circuit, and a reference numeral 33 is a water-interference/water-coexistence-influence correction arithmetic operation circuit (hereinafter simply referred to as a correction arithmetic operation circuit), wherein the concentration arithmetic operation section 29 performs arithmetic operations for concentrations of CO and $CO_2$ as components to be measured and a concentration of water as an interference component on the basis of outputs of the detectors 21 to 24 and further uses the thus obtained concentrations to attain concentrations of CO and $CO_2$ corrected with respect to a water influence according to a procedure (described later) as shown in FIG. 4.

Figure 5:
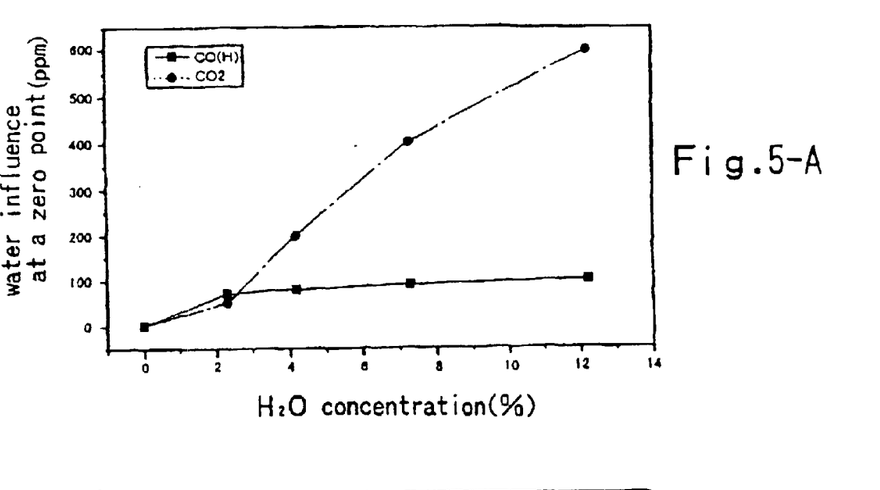
FIGS. 5A, 5B and 5C are graphs for describing water interference influences.

Next, description will be given of workings of the apparatus of infrared gas analysis 6 with the above construction below with reference to FIGS. 4 and 5. By driving the automobile 1 in which the apparatus for infrared gas analysis 6 and the personal computer 12 are mounted, an exhaust gas is expelled from the engine 2 and part of the exhaust gas is sampled as the sample gas SG through the branch connecting section 7 and the gas sampling flow path 8 to be fed into the cell 14 of the gas analysis section 6A in the apparatus for infrared gas analysis 6. In this case, since the branch connecting section 7 and the gas sampling flow path 8 are heated and thermally insulated at a prescribed temperature by the heater 11, components and water included in the taken sample gas SG are prevented from condensation.

In the gas analysis section 6A, the cell 14 is irradiated with infrared from the infrared source 18 and the sample gas SG passing through the gas sampling flow path 8 is fed into the cell 14 while the light chopper 19 rotates at a prescribed cycle and thereby, AC signals corresponding to concentrations of CO, $CO_2$ and $H_2O$, respectively, and an AC signal as a comparison signal are outputted from the detectors 21 to 24 and inputted to the synchronous commutator circuit 30.

Since, for example, a commutation synchronous signal s based on a rotation cycle of the light chopper 19 is inputted to the synchronous commutator circuit 30, measured AC signals corresponding concentrations are synchronously commutated by the synchronous signal s and further, smoothed in the smoothing circuit 31. Concentrations of CO, $CO_2$ and $H_2O$ are obtained by subtracting outputs relating to the concentrations of CO, $CO_2$ and $H_2O$ of the respective detectors 21, 22 and 23 from an output of the comparison circuit 24 in the subtractor circuit 32.

The concentrations of CO and $CO_2$ obtained by the above arithmetic operations have been influenced by water included in the sample gas SG, there is a necessity for performing correction with respect to the water influence to attain true concentrations (concentrations after correction with respect to the water influence). Description will be given of a principle and procedure of correction of a concentration below with reference to FIGS. 4 and 5.

Generally, in a nondispersive infrared gas analyzer (NDIR), since when CO and $CO_2$ are measured, an infrared absorption band (region) of $H_2O$ overlaps infrared absorption bands of CO and $CO_2$, a water interference at a zero point in each of systems of CO and $CO_2$ appear as shown in FIG. 5A.

Furthermore, a span point receive influences of a water interference and a water coexistence influence, and water influences appear as shown in FIG. 5B in this span. The water coexistence influence is a change in degree of infrared absorption itself of each of CO and $CO_2$ due to coexistence of water in a sample gas SG, and it is found that a water coexistence influence, as shown in FIG. 5C, has no dependency on a CO concentration, but a relation with a water concentration. A water coexistence influence is approximately proportional to a water concentration in the range of a water concentration of FIG. 5C. FIG. 5C shows an influence of water coexistence after subracting a water interference at a zero point from a water influence at a span point in each case.

Therefore, in the apparatus of infrared gas analysis 1 of the present invention, correlation is performed with respect to a water influence using a relationship between a water concentration and a water coexistence influence according to a procedure as shown in FIG. 4. FIG. 4, for example, shows a case where correction with respect to a water influence is performed on a CO concentration.

At first, a CO concentration (step S2a) and a water concentration (step S2b) are obtained on the basis of an output of the CO detector 21 (step S1a) and an output of the water detector 23 (step S1b), respectively, according to the procedure as described above. Note that the concentrations can be simultaneously obtained since the CO detector 21 and the water detector 23 are arranged optically in parallel to each other as shown in FIGS. 2 and 3.

Then, using a water concentration having been obtained in step S2b, the CO concentration having been obtained in step S2a is corrected with respect to a water interference at a zero point (step S3).

Subsequent to step S3, the CO concentration having been corrected with respect to a water interference at a zero point is further corrected using the water concentration having been obtained in step S2b with respect to a water coexistence influence since such a CO concentration, as described in FIG. 5C, has received a water coexistence influence almost linearly against a water concentration (step S4). In a case where a relationship between a water concentration and a water coexistence influence is linear in such away, a CO concentration can be corrected with respect to the water influence, for example, using the following expression (1):

$$(CO \text{ concentration after correction}) = ((CO \text{ concentration before correction}) - F1(w)) \times 100/(100 + k \cdot w) \quad (1)$$

where w is a water concentration,
F1 is a function calculated in FIG. 5A (for example, a quartic equation),
and k is an inclination of a straight line in FIG. 5C.

By this expression, a CO concentration after correction can be obtained in which both of a water interference at a zero point and a water interference at a span point (a water coexistence influence) have been excluded (step S5).

Note that needless to say that correction of a $CO_2$ concentration can be performed according to the procedure shown in FIG. 4.

In an apparatus of infrared gas analysis 6 of the present invention, as described above, a high precision concentration measurement can be performed in which after a water interference at a zero point is removed from each of measured values for CO and $CO_2$, which are components to be measured, a water coexistence influence is further removed from each of the measured values on the basis of a linear relationship between a water concentration and a water coexistence influence. Unlike a prior art method and apparatus, since no necessity arises for a pretreatment device such as a dehumidifier to be installed, not only a response speed in analysis is faster by a value corresponding thereto, but a construction of the apparatus as a whole becomes compact to save space, thereby enabling measurement at a low cost while saving power consumption. Furthermore, since measurement is performed in a state where a sample gas SG is heated and thermally insulated at a temperature or higher, no need arises for correction with respect to a water partial pressure.

In the above-mentioned apparatus of infrared gas analysis 6, since measurement is performed on CO and $CO_2$, which are components to be measured, and water, which is an interference component, with the one gas analysis section 6A, not only a delay for correction is cancelled, but constituent members are reduced in number as compared to a case that a water concentration is constituted so as to measured separately.

The above-mentioned apparatus of infrared gas analysis 6, because of compactness of its construction itself, is of a so-called vehicle mount type that can be mounted in the automobile 1, so exhaust gas measurement can be performed continuously in real time in a state where the automobile 1 is running.

Note that while in the above embodiment, arithmetic operations such as concentration calculation and correction of concentrations are performed in the apparatus for infrared gas analysis 6, the operations may be performed on the personal computer 12.

Figure 6:
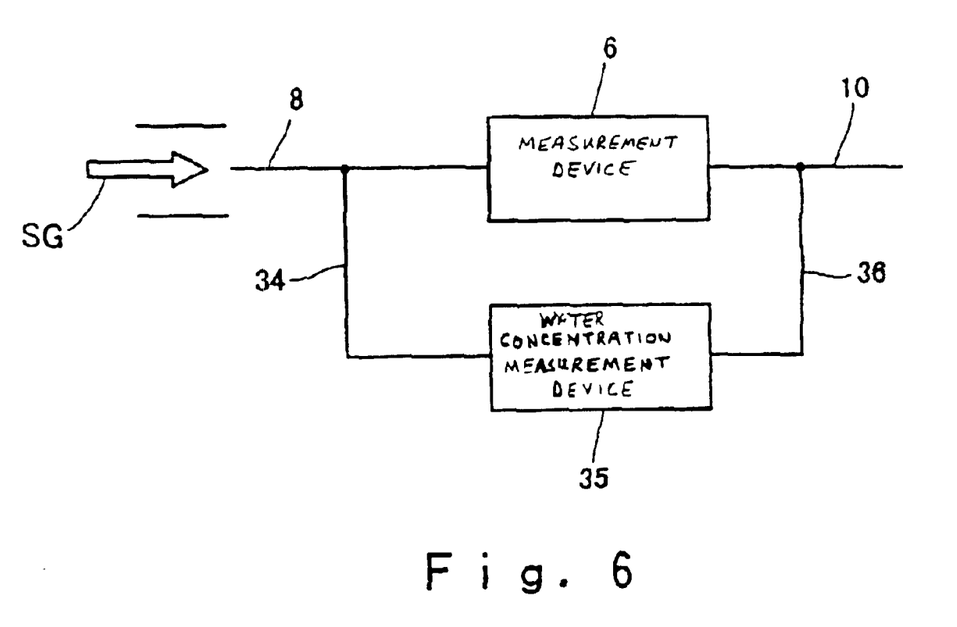
FIG. 6 is a diagram schematically showing a second embodiment of the present invention.

Note that while in the above embodiment, measurement is performed on CO, $CO_2$, which are components to be measured, and water, which is an interference component, with the one gas analysis section 6A, measurement may be performed on CO, $CO_2$ and so on, which are components to be measured included in a sample gas SG, with a measurement device, separately from measurement on water included in the sample gas SG with another measurement device in such a way that as in the second embodiment shown in FIG. 6, the branch flow path 34 is connected to a the gas sampling flow path 8, a water concentration measurement device 35 is provided in the branch flow path 34 and a flow path 36 at the side downstream of the water concentration measurement device 35 is connected to the exhaust flow path 10.

Moreover, the detection section 20 in the gas analysis section 6A may be equipped with detectors for measuring plural kinds of specific components such as HC in addition to the above described CO and $CO_2$, or alternatively, may be designed so as to measure a single specific component.

While in the first and second embodiments, the branch flow path (constituted of the flow paths 8 and 10) sampling part of an exhaust gas flowing in the exhaust pipe 3 is provided to the exhaust pipe 3 connected to the engine 2 and the gas analysis section 6A including the cell 14, the infrared source 18 and the detection section 20 is provided in the branch flow path, a construction may be adopted in which the exhaust pipe 3 itself works as a cell and the infrared source 18 and the detection section 20 are installed oppositely to each other in the exhaust pipe 3. Description will be given of an example configuration of such an apparatus for infrared gas analysis as a third embodiment below with reference to FIGS. 7 and 8.

Figure 7:
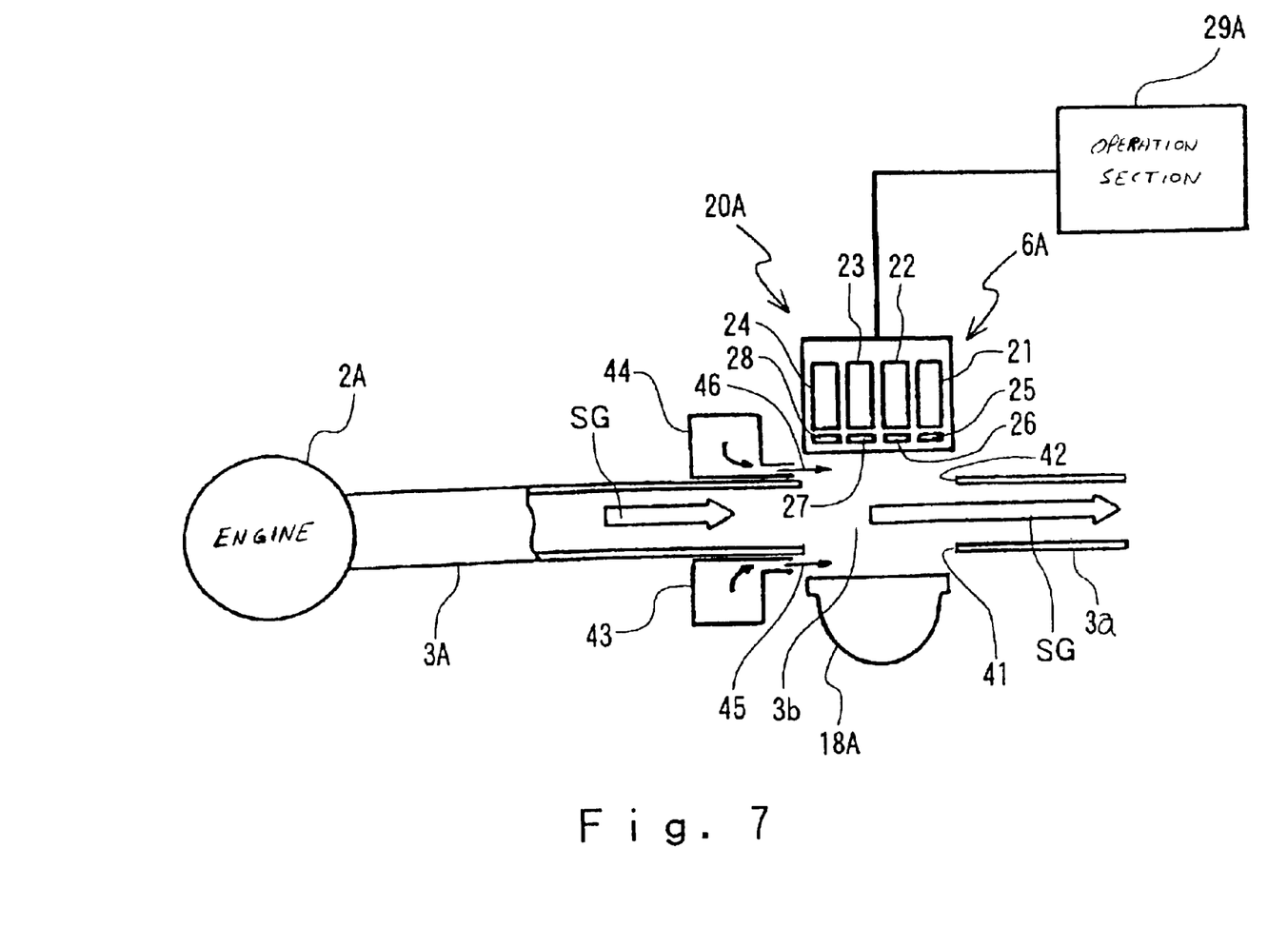
FIG. 7 is a diagram schematically showing a third embodiment of the present invention.

At first, in FIG. 7, a reference numeral 2A indicates an engine of an automobile (not shown) and a reference numeral 3A indicates an exhaust pipe (one example of a pipe) in the sectional shape of, for example, a circle connected to the engine 2A. Reference numerals 41 and 42 are openings formed in a pipe wall 3a of the exhaust pipe 3A at a proper position (in the side downstream thereof in the example shown in the FIG.). To be detailed, the openings 41 and 42 are formed on one diameter of the pipe wall 3a oppositely to each other. An infrared source 18A is provided outside the one opening 41 (outside the exhaust pipe 3A) so as to face the opening 41, while outside the other opening 42, a detection section 20A is provided so as to face the opening 42. The infrared source 18A and the detection section 20A are constructed similarly to the infrared source 18 and the detection section 20 in the first embodiment, the same reference numerals as those in FIG. 2 are attached to corresponding constituents and descriptions thereof are omitted.

Furthermore, reference numerals 43 and 44 indicate fans installed so as to be located at the pipe wall 3a in the side (the engine 2A side) upstream of the openings 41 and 42 and the fans 43 and 44 are to form air curtains 45 and 46 between the pipe wall 3a and each of the infrared source 18A and the detection source 20A.

In the apparatus for infrared gas analysis of the third embodiment shown in FIG. 7, a cell is a space 3b itself between the openings 41 and 42 formed oppositely to each other in the exhaust pipe 3A in which an exhaust gas flows from the engine 2A, the infrared source 18A is provided at one end side of the cell 3b, while at the other end side thereof, the detection section 20A is provided, thus forming a gas analysis section 6A. Note that in FIG. 7, a reference numeral 29A indicates a concentration arithmetic operation section performing a concentration arithmetic operation on the basis of outputs from the detection section 20A, which workings are the same as the concentration arithmetic operation section 29 in the first embodiment.

In the thus constructed apparatus for infrared gas analysis, the exhaust gas from the engine 2A flows through the cell 3b as the sample gas SG, which is irradiated with an infrared beam from the infrared source 18A such that the infrared beam traverses the sample gas SG while chopping the infrared beam at a prescribed cycle. The infrared beam with which the sample gas SG is irradiated impinges on detectors 21 to 24 of the detection section 20A and outputs from the detectors 21 to 24 are inputted to the concentration arithmetic section 29A to receive arithmetic operations similar to the first embodiment in the concentration arithmetic operation section 29A. In an apparatus for infrared gas analysis of the second embodiment as well, therefore, there can be attained an action and effect similar to those of the apparatus for infrared gas analysis in the first embodiment, that is the action and effect as described above. In this embodiment, an excellent action and effect described below are also further exerted.

That is, since part of the exhaust pipe 3A through which the exhaust gas flows works as the cell 3b of the apparatus for infrared gas analysis, absolutely no necessity arises for a gas sampling system including a device, a flow path and so on for sampling the sample gas SG, thereby simplifying a construction of the apparatus by a degree corresponding thereto. No requirement for the gas sampling system eliminates a delay in indication of the analyzer and reduction in speed of a rise in indication thereof. Since the water traveled up to the gas analysis section repeating adsorption and desorption on the wall surface of the pipe in the gas sampling system when a water concentration in the sample gas SG was measured in a prior art procedure, so a speed of a rise in indication of the analyzer was inevitably slowed, while in this embodiment, no such an influence exists altogether without performing gas sampling.

In a case where water is included in the sample gas SG, a water influence is problematic in an apparatus for infrared gas analysis of a linear interpolation type because of impossibility to remove water, while in this embodiment, correction can be performed with respect to a water influence in real time since the water detector 23 is installed in the detection section 20A.

Furthermore, since the air curtains 45 and 46 are formed between the pipe wall 3a and each of the infrared source 18A and the detection section 20A by the fans 43 and 44, direct contact of the sample gas SG with a window of the infrared source 18A, the optical filters 25 to 28 and windows of the detectors 21 to 24 in the detection section 20A is effectively prevented, thereby enabling stable acquirement of desired concentration detection outputs over long term use.

Figure 8:
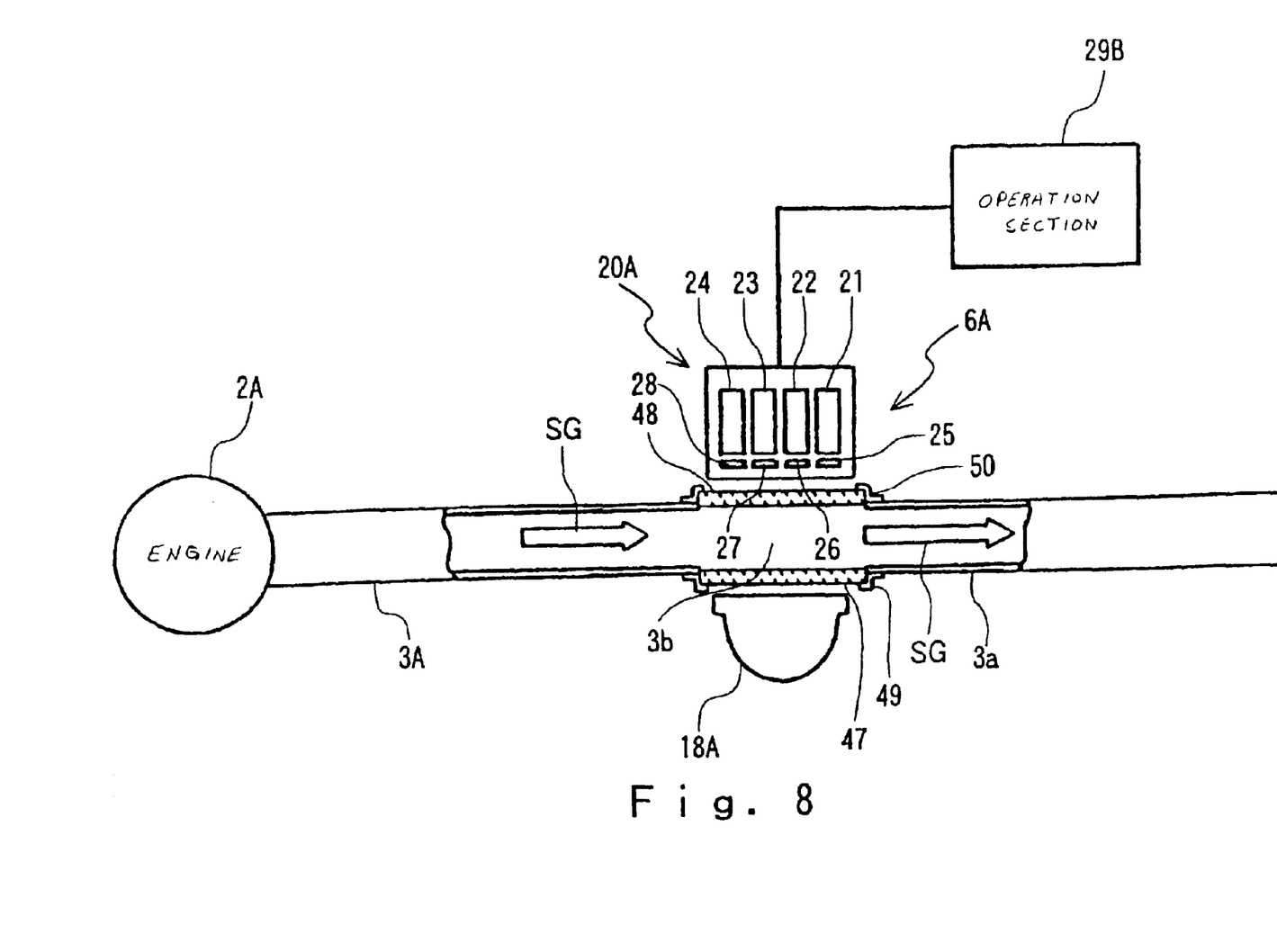
FIG. 8 is a diagram schematically showing a modification of the third embodiment of the present invention.

Since in the apparatus for infrared gas analysis shown in FIG. 7, the openings 41 and 42 are formed in the exhaust pipe 3A and the infrared source 18A is provided oppositely to the one opening 41, and the detection section 20A is provided oppositely to the other opening 42, the fans 43 and 44 for forming the air curtains 45 and 46 flowing along the openings 41 and 42 are installed, while as shown in FIG. 8, optical windows 47 and 48 made of infrared transmissible material may be mounted at the openings 41 and 42 for sealing the openings 41 and 42 using proper sealing materials 49 and 50. In this case, the infrared source 18A and the detection section 20A may be mounted in close contact with the respective optical windows 47 and 48.

In the apparatus for infrared gas analysis shown in FIG. 8, needless to say that there is exerted an effect similar to that of the apparatus for infrared gas analysis in FIG. 7. In the apparatus shown in FIG. 8, there is no fear that the exhaust gas leaks out from the windows 41 and 42 formed in the exhaust pipe 3A at an intermediate position of the entire length thereof, therefore an installment site of the gas analysis section 6A is arbitrary.

While in the embodiments shown in respective FIGS. 7 and 8, the gas analysis section 6A is formed in the exhaust pipe 3A directly connected to the engine 2A, a construction may be adopted in which an additional pipe is further connected to the exhaust pipe 3A in series therewith and the gas analysis section 6A is provided in the additional pipe.

Note that while in the above three embodiments, arithmetic operations such as a concentration calculation and a concentration correction are performed in the apparatus for infrared gas analysis 6, the arithmetic operations may be performed in a proper arithmetic operation device (not shown) such as a personal computer. The engines 2 and 2A in the embodiments may be any of one mounted in an automobile in running on a road surface, one mounted in an automobile placed on a chassis dynamo and one itself placed on an engine dynamo.

In the above embodiment, there are shown cases where the sample gas SG is introduced into the cell 14 provided in a flow path in parallel to the exhaust pipe 3, and where the sample gas SG passes through the exhaust pipe 3A, wherein correction is performed with respect to an interference influence of water exerting an influence on measurement of a specific component in the sample gas SG, thereby achieving measurement of a concentration of a desired component with good precision, while the present invention is not limited to those, but can be used in so-called remote sensing for measuring a specific component in a specific region or space.

Figure 9:
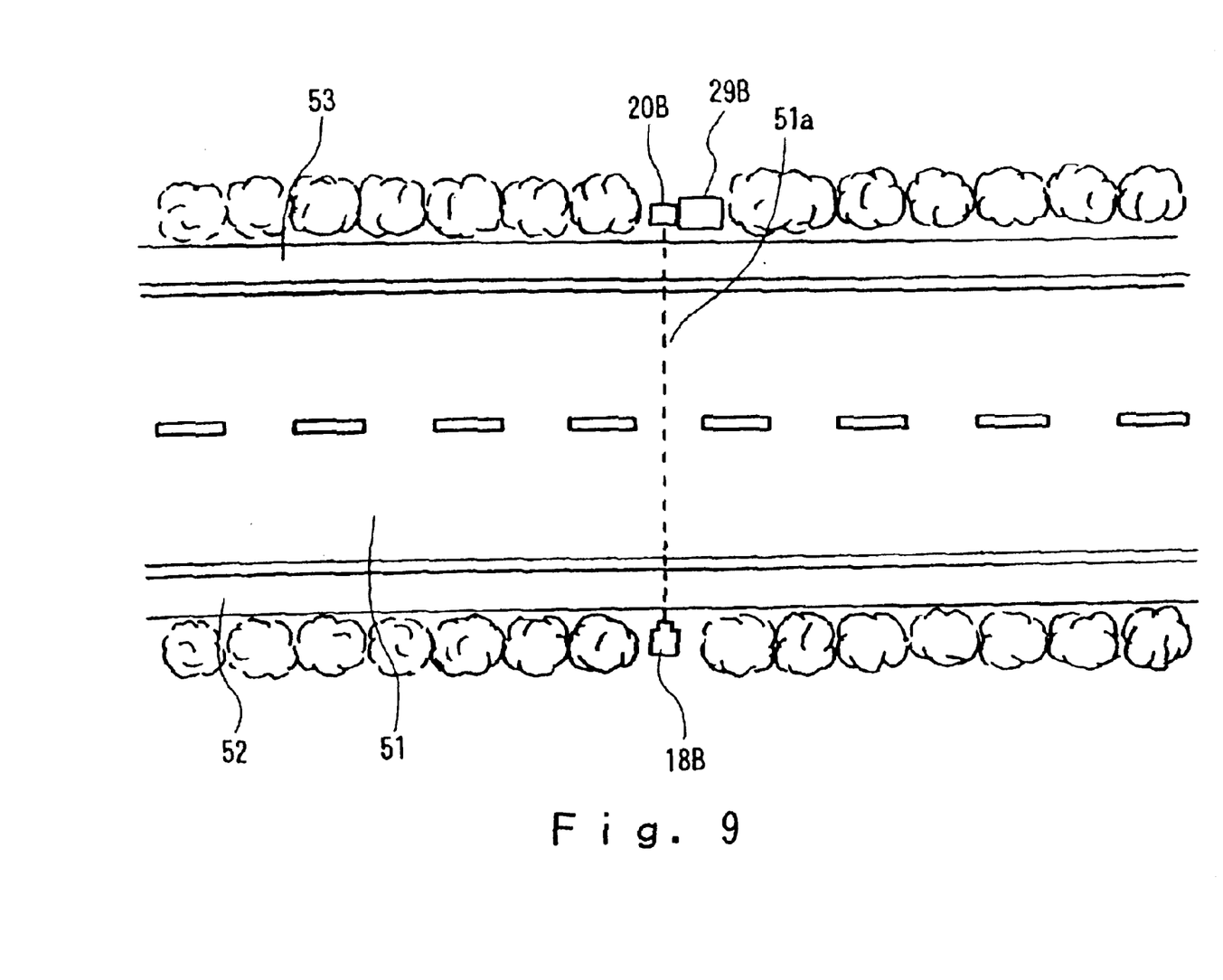
FIG. 9 is a representation schematically showing a fourth embodiment of the present invention.

That is, FIG. 9 shows an example of the remote sensing and in the FIG., a reference numeral 51 indicates a road on which a vehicle such as an automobile runs and reference numerals 52 and 53 indicate sidewalks on both sides of the road. Of the sidewalks 52 and 53, for example, an infrared source 18B is provided on the one sidewalk 52, and a detection section 20B and a concentration arithmetic operation section 29B are provided on the other sidewalk 53. The infrared source 18B, the detection section 20B and the concentration arithmetic operation section 29B are of constructions similar to those of the infrared source 18, the detection section 20 and the concentration arithmetic operation section 29 shown in FIG. 2. In this case, the infrared source 18B and the detection section 20B are located oppositely to each other and a space above the road 51a between the infrared source 18B and the detection section 20B works as a cell. Note that preferably the infrared source 18B and the detection section 20B are disposed so as not to be so much high above the road surface and so as not to disturb passage of humans and others on the sidewalks.

In the above configuration, for example, if an exhaust gas expelled from an automobile when running on the road is present in the space portion 51a, the exhaust gas serves as a sample gas and the exhaust gas is irradiated with an infrared beam emitted from the infrared source 18B such that the infrared beam traverses the sample gas while chopping the infrared beam at prescribed cycle. The infrared beam with which the sample gas is irradiated impinges on detectors (not shown) of the detection section 20B, and outputs from the detectors are inputted to the concentration arithmetic operation section 29B and receive arithmetic operations similar to the first embodiment therein in this concentration arithmetic operation section 29B.

In the fourth embodiment shown in FIG. 9 as well, correction is performed with respect to an influence of water included in the sample gas to thereby enable measurement of concentrations of desired components to be measured with good precision, and preferably perform a so-called remote sensing.

In a method and apparatus for infrared gas analysis of the present invention, as described above, correction is performed with respect to an influence of water included in a sample gas, though with a simple construction to thereby, enable measurement of concentrations of desired components to be measured with good precision.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method of infrared gas analysis for use with a gas analysis section including a cell with an infrared source at one end of the cell and a detection section at the other end of the cell, the method comprising:

feeding a sample gas to the gas analysis section;

measuring a concentration of a component in the sample gas;

measuring a concentration of water in the sample gas;

correcting the component concentration measurement with respect to water interference at a zero point; and correcting the component concentration measurement with respect to water influence in coexistence to determine a corrected measurement that is corrected with respect to water interference at the zero point and water influence in coexistence.

2. The method of claim 1 wherein water interference at a zero point and water influence in coexistence are corrected on the basis of measured concentration of water in the sample gas.

3. The method of claim 1 wherein the gas analysis section is a single gas analysis section and wherein measuring the component concentration and measuring the water concentration take place at the single gas analysis section.

4. A method of infrared gas analysis for use with a pipe through which a sample gas flows having two openings with an infrared source installed so as to face one opening thereof and a detection section installed at the other opening thereof, the method comprising:

measuring a concentration of a component in the sample gas based on detection outputs obtained when the sample gas is irradiated with an infrared beam passing through the two openings;

measuring a concentration of water in the sample gas based on detection outputs obtained when the sample gas is irradiated with an infrared beam passing through the two openings;

correcting the component concentration measurement with respect to water interference at a zero point; and correcting the component concentration measurement with respect to water influence in coexistence to determine a corrected measurement that is corrected with respect to water interference at the zero point and water influence in coexistence.

5. The method of claim 4 wherein an air curtain is formed outside an opening of the pipe.

6. The method of claim 4 wherein an optical window with infrared transmissability is installed at an opening of the pipe.

7. A method of infrared gas analysis for use with an infrared source and a detection section positioned such that an emitted infrared beam from the infrared source traverses a sample gas prior to reception by the detection section, the method comprising:

measuring a concentration of a component in the sample gas;

measuring a concentration of water in the sample gas;

correcting the component concentration measurement with respect to water interference at a zero point; and correcting the component concentration measurement with respect to water influence in coexistence to determine a corrected measurement that is corrected with respect to water interference at the zero point and water influence in coexistence.

8. An apparatus for infrared gas analysis, the apparatus comprising:

a gas analysis section for receiving a sample gas, the gas analysis section including a cell;

an infrared source at one end of the cell;

a detection section at the other end of the cell; and an operation section for measuring a concentration of a component in the sample gas, for measuring a concentration of water in the sample gas, for correcting the component concentration measurement with respect to water interference at a zero point, and for correcting the component concentration measurement with respect to water influence in coexistence to determine a corrected measurement that is corrected with respect to water interference at the zero point and water influence in coexistence.

9. The apparatus of claim 8 wherein water interference at a zero point and water influence in coexistence are corrected on the basis of measured concentration of water in the sample gas.

10. The apparatus of claim 8 wherein the gas analysis section is a single gas analysis section and wherein measuring the component concentration and measuring the water concentration take place at the single gas analysis section.

11. A apparatus of infrared gas analysis, the apparatus comprising:

a pipe through which a sample gas flows having two openings;

an infrared source installed so as to face one opening of the pipe;

a detection section installed at the other opening of the pipe; and an operation section for measuring a concentration of a component in the sample gas based on detection outputs obtained when the sample gas is irradiated with an infrared beam passing through the two openings, for measuring a concentration of water in the sample gas based on detection outputs obtained when the sample gas is irradiated with an infrared beam passing through the two openings, for correcting the component concentration measurement with respect to water interference at a zero point, and for correcting the component concentration measurement with respect to water influence in coexistence to determine a corrected measurement that is corrected with respect to water interference at the zero point and water influence in coexistence.

12. The apparatus of claim 11 wherein an air curtain is formed outside an opening of the pipe.

13. The apparatus of claim 11 wherein an optical window with infrared transmissability is installed at an opening of the pipe.

14. A apparatus for infrared gas analysis, the apparatus comprising:

an infrared source;

a detection section positioned such that an emitted infrared beam from the infrared source traverses a sample gas prior to reception by the detection section; and an operation section for measuring a concentration of a component in the sample gas, for measuring a concentration of water in the sample gas, for correcting the component concentration measurement with respect to water interference at a zero point, and for correcting the component concentration measurement with respect to water influence in coexistence to determine a corrected measurement that is corrected with respect to water interference at the zero point and water influence in coexistence.

* * * * *